United States Patent [19]

Hausheer

[11] Patent Number: 5,922,714
[45] Date of Patent: Jul. 13, 1999

[54] COMBINATION OF MDAM AND 5-FLUOROPYRIMIDINES FOR TREATING CANCER

[75] Inventor: Frederick H. Hausheer, Boerne, Tex.

[73] Assignee: BioNumerik Pharmaceuticals, Inc., San Antonio, Tex.

[21] Appl. No.: 08/996,540

[22] Filed: Dec. 23, 1997

Related U.S. Application Data

[60] Provisional application No. 60/034,364, Dec. 26, 1996.

[51] Int. Cl.[6] .......................... A61K 31/495; A61K 31/50; A61K 31/505
[52] U.S. Cl. ............................................ 514/249; 514/274
[58] Field of Search ....................................... 514/249, 274

[56] References Cited

U.S. PATENT DOCUMENTS

| 4,996,207 | 2/1991 | Nair et al. | 514/258 |
| 5,550,128 | 8/1996 | Nair et al. | 514/249 |

OTHER PUBLICATIONS

Schmid et al., Cancer Treat. Rep., 71(7–8), 727–32 Abstract Only, 1987.

*Primary Examiner*—Jerome D. Goldberg
*Attorney, Agent, or Firm*—Thomas J. Dodd

[57] ABSTRACT

A method of treating patients with cancer which includes administering to a patient in need of such treatment an effective amount of a combination of γ-methylene-10-deazaaminopterin, and either a 5-fluoropyrimidine or S-1.

4 Claims, No Drawings

COMBINATION OF MDAM AND 5-FLUOROPYRIMIDINES FOR TREATING CANCER

This application claims benefit of Provisional Appl. 60/084,364 filed Dec. 26, 1996.

FIELD OF THE INVENTION

This invention relates to a novel drug combination chemotherapy for patients with cancer, which therapy includes the administration of an effective amount of MDAM (4-amino-4-deoxy-γ-methylene-10-deazaaminopterin), in combination with a 5-Fluoropyrimidine, such as 5-FU (5-Fluorouracil), UFT (a combination of a 5-FU prodrug and uracil), S-1 (a combination of three antitumor compounds), Capecitabine, or the like. The administration of the combination may be effected as a single dose, or the combination may be administered separately.

BACKGROUND OF THE INVENTION
1. Prior uses of MDAM, Methotrexate and the 5-Fluoropyrimidines MDAM (4-amino-4-deoxy-γ-methylene-10-deazaaminopterin), is a potent inhibitor of dihydrofolate reductase (DHFR) and is currently in clinical trials in the United States as a treatment for human solid tumors and leukemias. MDAM is described and claimed in U.S. Pat. Nos. 4,996,207; 5,073,554; and 5,260,296; and other patents, both in the United States and abroad.

MDAM is an analogue of Methotrexate (Amethopterin), a DHFR inhibitor which has been in use for many years to treat various types of human cancer and also has been prescribed as a treatment for some forms of rheumatoid arthritis, psoriasis and asthma. As described in the above listed MDAM patents, Methotrexate (MTX) undergoes polyglutamylation which can result in significant patient toxicity, particularly myelosuppression and GI toxicity.

MDAM does not undergo the polyglutamylation commonly associated with Methotrexate, and has a higher therapeutic index than MTX. Further, MDAM is not as susceptible to MDR or MRP resistance and is more effective in treating several types of drug-resistant cancers.

5-Fluoropyrimidines, particularly 5-FU (5-fluorouracil) and the like, are widely used antitumor agents which have also been used for a number of years to treat various types of human cancers. 5-FU has been used both alone and in combination with other chemotherapeutic agents, particularly with Methotrexate to treat a number of different types of tumors and leukemias. 5-FU inhibits thymidylate synthetase and other enzymes to interfere with DNA synthesis, is directly incorporated into DNA and RNA, and also blocks formation of uracil phosphatase to inhibit RNA synthesis as well.

As with MTX, the major toxic effects of 5-FU are also myelosuppression and GI toxicity, as well as other toxicities. 5-FU is also susceptible to drug resistant strains of cancers, and has a low therapeutic index if used alone.

UFT is a combination of a 5-FU prodrug (N-furan-2-yl-5-fluorouracil), and uracil in a 1:4 ratio. Capecitabine is a novel compound currently in clinical trials throughout the world, and has exhibited oral efficacy against certain tumors.

S-1 (A combination of 5-FU (or the furanyl prodrug listed above):potassium oxonate:2,4-dihydroxy-5-chloropyridine (CDHP), in a 1:1:0.4 ratio) is a recently developed antitumor agent. A study was conducted recently which compared the activity of S-1 with the activity of UFT (5-FU:Uracil, 1:4), against a common human cancer (human colorectal adenocarcinoma KM12C). Shirasaka, et al, "Antitumor Activity of 1 M Tegafur- 0.4 M 5-Chloro-2,4-dihydroxypyridine- 1 M Potassium Oxonate (S-1) against Human Colon Carcinoma Orthotopically Implanted into Nude Rats," *Cancer Research*, vol. 26, pg. 2602 (1996). S-1 was found to be significantly more effective against this tumor type than either 5-FU or UFT alone.

2. Combinations of Chemotherapeutic Drugs

Clinicians have consistently tried to improve the response of cancer patients by combining two or more antitumor drugs into a single therapeutic regimen. By combining two or more chemotherapeutic agents, most often with different mechanisms of action, the clinician is able to both increase the therapeutic index of the individual drugs, and at the same time reduce the toxic effects to the patient.

A relevant example (with regard to the subject matter of this invention) of combination chemotherapy has been the concurrent administration of Methotrexate and 5-FU. A number of studies have been conducted which explored the benefits (and the drawbacks) of combination therapy utilizing these two well-known drugs, and the references which disclose the results of these studies are included in the List of References, supra.

A number of other combinations have also been employed by clinicians and researchers in their efforts to treat various forms of cancer in various stages of the disease. The focus of these combination efforts is to increase the therapeutic index of the individual drugs, hopefully in a synergistic fashion, while at the same time decreasing the risk of harmful effects to the patient from the use of such drugs. In the case of Methotrexate (MTX)/5-FU combination therapy, the synergistic combination involved the pretreatment of the cancer cells with MTX, followed by a treatment with 5-FU to enhance cancer cell kill. This combination was time and sequence dependent, and deviation from the preferred schedule of treatment actually decreased the effects of the combination as compared with individual results.

The number of combination therapies which have been used to treat various forms of cancer is very large and may be found throughout the literature. This is due to the large number of tumor cell lines which have been identified, and to the ultimate goals in any treatment program-providing better quality of life, while controlling the disease with the safety of the patient foremost.

SUMMARY OF THE INVENTION

The treatment method of this invention involves a combination therapy which utilizes two or more known antitumor agents. One of these agents is MDAM, or an analogue thereof. The second agent is a 5-fluoropyrimidine. The method involves the combination treatment of a patient with cancer, with an effective amount of MDAM and an effective amount of a 5-fluoropyrimidine. The combination treatment of this invention is not schedule dependent, and the combination may be administered simultaneously, or the drugs may be administered individually, in time-spaced doses.

The combination therapy is effective in controlling and reducing tumors of at least three different cell lines which have heretofore exhibited resistance to chemotherapeutic agents. Experiments were performed in vitro with the HCT/WT, HCT/DW2 and HCT8/FL2H human colon carcinoma cell lines. The synergistic results, outlined below, illustrate the potentiation effects of the combination therapy of this invention.

It is a principal object of this invention to provide a method of treating cancer by administering an effective dose of MDAM, or an analogue thereof, in combination with a 5-fluoropyrimidine.

Another object of this invention is to provide for a method of increasing the antitumor efficacy of MDAM and a 5-fluoropyrimidine, while at the same time maintaining a reasonable margin of patient safety and low levels of toxicity.

Another object of this invention is to provide a chemotherapeutic treatment regimen for controlling heretofore drug-resistant tumors.

Other objects will become apparent upon a reading of the following specification.

DESCRIPTION OF THE PREFERRED EMBODIMENTS

The preferred embodiments herein described are not intended to be exhaustive nor to limit the invention to the precise forms or details disclosed. They are chosen and described to best explain the principles of the invention and the application and practical use to enable others skilled in the art to follow its teachings.

The treatment method of this invention involves the administration of 1) MDAM; and 2) a 5-fluoropyrimidine, preferably one of the following: a) 5-fluorouracil (5-FU); b) UFT; c) Capecitabine; or d) S-1, to subjects (human/animals) with cancer. The structures of the drugs employed in this invention are as follows:

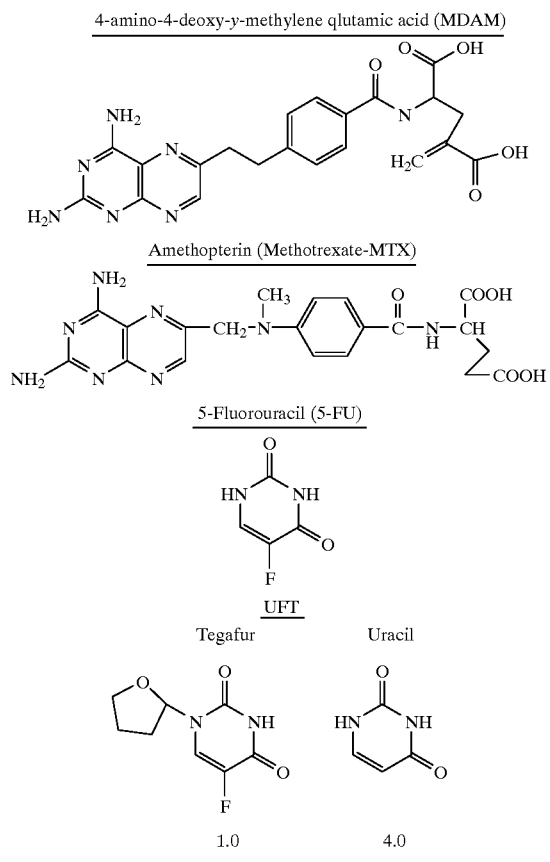

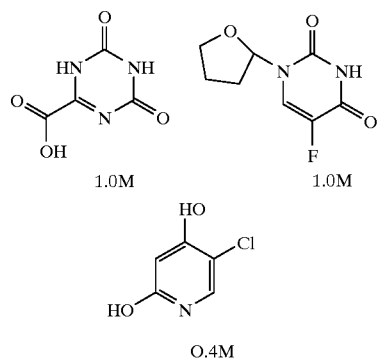

The treatment method of this invention has been proven effective against a common drug-resistant tumor cell line which has heretofore exhibited resistance to treatment with Methotrexate and 5-FU, both individually and in combination. This tumor line, identified as the HCT8 line, has many identified subgroups, three of which are commonly known as HCT8/FL2H, HCT8/WT, and HCT8/DW2. HCT is a common adenocarcinoma which has proven extremely difficult to treat, particularly due to its ability to resist control by known drugs.

Experiments were designed to measure the effectiveness of the treatment method of this invention against the three cell lines identified above. In each experiment (all of which were performed in vitro), the drugs (MDAM, MTX, 5-FU, UFT, and S-1) were delivered individually to a culture containing a predetermined number of tumor cells, and the efficacy measured. Combinations of MDAM, and either 5-FU or S-1 were then administered and efficacy was again measured. In all experiments against all three cell lines, the combination therapy proved to be significantly more effective than individual drug therapy. The protocol for each of the experiments and the results thereof are disclosed below.

The protocol for the treatment of each cell line was the same in each experiment as follows:

1. Cells were seeded (800 cells/well/100 $\mu$L) into plates (96 wells each), with the HCT8/FL2H cells pretreated with about 200 $\mu$M 5-FU and 20 $\mu$M leucovorin (LV) for 2 hours, then cultured 10 times in the presence of 20 $\mu$M LV, which procedure was repeated 10 times.

2. Some wells were treated individually with: a) MTX; b) MDAM; c) 5-FU; and d) S-1. Concentrations of each compound used are described in the tables, supra. 3. Some wells were treated with a co-administered dosage of MTX/5-FU, MTX/S-1, MDAM/5-FU, or MDAM/S-1. The exact procedures and concentrations of each drug are described in the tables.

4. Some wells were treated with one of the MTX or MDAM/5-FU or S-1 combinations (see #3) for a predetermined period of time, after which the drugs were removed and the well treated with MDAM or MTX individually.

5. Cell counts were recorded for each well by a standard cell counting device, and percentage of cells surviving was measured. Since the doubling rate for each of the cell lines is well-known (T×2~19 hours), the percentage of cell survival is easily calculated by controlling the time intervals of the experiments. Further, the half-lives of the drugs used are also well-known values. The treatment phase of the experiments was designed to correlate with the time which the drugs are active in the body, so as to closely duplicate the action of the drugs in the body.

The following examples demonstrate the specific utility of this invention. They are disclosed for illustrative purposes only, and do not limit the invention to the precise concentrations, time schedules or other details therein.

EXAMPLES 1–8

Individual Drug Treatments

In each of Examples 1–8, the cells were exposed to each of the four drugs individually for a period of 48 hours. After seeding of the cells into the individual wells in the concentrations described above, the wells were allowed to stand for 24 hours, then the drugs were added in the concentrations shown in Table 1. The drugs remained in the wells for 48 hours, after which they were washed out and the wells allowed to sit for 24 more hours. Cell count was then taken and the percentage of cells surviving was calculated. Three experiments were performed at each of three concentrations (10 nM, 5 nM and 1 nM) for MDAM and MTX, and the results averaged. Three experiments were performed at a single concentration (5 µM) for 5-FU and S-1, and the results averaged. The results of these examples are shown below in Table 1.

Example 1—MDAM vs. HCT8/WT
Example 2—MTX vs. HCT8/WT
Example 3—5-FU vs. HCT8/WT
Example 4—S-1 vs. HCT8/WT
Example 5—MDAM vs. HCT8/FL2H
Example 6—MTX vs. HCT8/FL2H
7—5-FU vs. HCT8/FL2H
8—S-1 vs. HCT8/FL2H

TABLE 1

| Example # | % Cells Surviving | | | |
|---|---|---|---|---|
| | 10 nM | 5 nM | 1 nM | 5 µM |
| 1 | 46 | 79 | 90 | |
| 2 | 69 | 97 | 95 | |
| 3 | | | | 64 |
| 4 | | | | 43 |
| 5 | 50 | 84 | 94 | |
| 6 | 63 | 100 | 98 | |
| 7 | | | | 69 |
| 8 | | | | 50 |

EXAMPLES 9–24

Combination Treatments of 48 Hours MDAM or MTX with 24 Hours 5-FU or S-1

The following examples explored the effects of cell exposure to 48 hours of MDAM or MTX, in combination with a 24 hour exposure to either 5-FU or S-1. In all examples, cells were seeded into the wells as described in Examples 1–8, left to stand for 24 hours. In examples 9–16, the second drug (5 µM 5-FU or 5 µM S-1) was added concurrently with the MDAM or MTX 10 nM, 5 nM, 1 nM), all drugs were washed out after 24 hours, then an identical concentration of MDAM or MTX was added. In examples 17–24, after adding MDAM or MTX (10 nM, 5 nM, 1 nM), the wells were allowed to stand for 24 hours, then the second drug was added to the well (5 µM), and the combination allowed to stand for 24 more hours, at which time the drugs were washed out, the wells allowed to stand for 24 additional hours. The cells were then counted and percentage of cell survival was calculated. Three experiments were performed with each example, and the results averaged, and are seen below in Table 2.

| Example 9- | 48 MDAM | 0–24 5-FU | HCT8/WT |
| Example 10- | 48 MTX | 0–24 5-FU | HCT8/WT |
| Example 11- | 48 MDAM | 0–24 S-1 | HCT8/WT |
| Example 12- | 48 MTX | 0–24 S-1 | HCT8/WT |
| Example 13- | 48 MDAM | 0–24 5-FU | HCT8/FL2H |
| Example 14- | 48 MTX | 0–24 5-FU | HCT8/FL2H |
| Example 15- | 48 MDAM | 0–24 S-1 | HCT8/FL2H |
| Example 16- | 48 MTX | 0–24 S-1 | HCT8/FL2H |
| Example 17- | 48 MDAM | 24–48 5-FU | HCT8/WT |
| Example 18- | 48 MTX | 24–48 5-FU | HCT8/WT |
| Example 19- | 48 MDAM | 24–48 S-1 | HCT8/WT |
| Example 20- | 48 MTX | 24–48 S-1 | HCT8/WT |
| Example 21- | 48 MDAM | 24–48 5-FU | HCT8/FL2H |
| Example 22- | 48 MTX | 24–48 5-FU | HCT8/FL2H |
| Example 23- | 48 MDAM | 24–48 S-1 | HCT8/FL2H |
| Example 24- | 48 MTX | 24–48 S-1 | HCT8/FL2H |

TABLE 2

| Example # | % Cells Surviving | | |
|---|---|---|---|
| | 10 nM | 5 nM | 1 nM |
| 9 | 41 | 60 | 74 |
| 10 | 56 | 72 | 74 |
| 11 | 46 | 54 | 60 |
| 12 | 49 | 55 | 61 |
| 13 | 49 | 68 | 76 |
| 14 | 57 | 74 | 78 |
| 15 | 48 | 60 | 61 |
| 16 | 56 | 61 | 61 |
| 17 | 38 | 59 | 73 |
| 18 | 50 | 67 | 71 |
| 19 | 41 | 65 | 60 |
| 20 | 54 | 61 | 60 |
| 21 | 40 | 71 | 75 |
| 22 | 55 | 80 | 80 |
| 23 | 47 | 68 | 66 |
| 24 | 56 | 65 | 65 |

EXAMPLES 25–36

Treatment With 24 Hours MDAM/MTX and 6 or 12 hours 5-FU

These examples explore the effects of both a shortened exposure time of the cells to MDAM/MTX, and a shorter and varied exposure to 5-FU. Examples 25–32 depict the results of a 24 hour exposure to MDAM (MTX) combined with a 6 hour exposure to 5-FU, which is begun at 0, 6, 12 and 18 hours following administration of the MDAM (MTX). Examples 33–36 depict the results of a 24 hour exposure to MDAM (MTX) combined with a 12 hour exposure to 5-FU which is either coadministered or administered 12 hours after MDAM (MTX). Total exposure time for this set of examples is 72 hours (24 hours culturing, 24 hours drug treatment, 24 hours after drugs are washed out). The surviving cells are counted and the percentage of cells surviving is calculated as in the above examples. Percentage of cells surviving is depicted in Table 3, below. All cells assayed were HCT8/WT. MDAM was administered in each of three concentrations (1000 nM, 100 nM, and 10 nM), MTX at 100 nM and 10 nM, and 5-FU was administered at 10 µM. Each percentage is the average of two individual experiments.

| Example 25- | 24 MDAM | 0–6 5-FU |
| Example 26- | 24 MTX | 0–6 5-FU |
| Example 27- | 24 MDAM | 6–12 5-FU |
| Example 28- | 24 MTX | 6–12 5-FU |
| Example 29- | 24 MDAM | 12–18 5-FU |
| Example 30- | 24 MTX | 12–18 5-FU |
| Example 31- | 24 MDAM | 18–24 5-FU |
| Example 32- | 24 MTX | 18–24 5-FU |
| Example 33- | 24 MDAM | 0–12 5-FU |
| Example 34- | 24 MTX | 0–12 5-FU |
| Example 35- | 24 MDAM | 12–24 5-FU |
| Example 36- | 24 MTX | 12–24 5-FU |

TABLE 3

| Example # | 1000 nM | 100 nM | 10 nM |
|---|---|---|---|
| 25 | 19.0 | 26.3 | 55.4 |
| 26 |  | 15.3 | 64.8 |
| 27 | 16.7 | 21.2 | 50.4 |
| 28 |  | 14.1 | 59.1 |
| 29 | 12.3 | 18.2 | 40.7 |
| 30 |  | 12.1 | 60.3 |
| 31 | 11.2 | 14.4 | 32.4 |
| 32 |  | 10.5 | 45.5 |
| 33 | 15.5 | 21.4 | 56.3 |
| 34 |  | 12.6 | 62.9 |
| 35 | 9.4 | 12.4 | 30.1 |
| 36 |  | 9.1 | 47.8 |

EXAMPLES 37–48
Treatment With 24 Hours 5-FU and 6 or 12 Hours of MDAM or MTX The same reaction conditions were carried out as in examples 25–36, with the order of administration of the drugs reversed.

| Example 37- | 24 5-FU | 0–6 MDAM |
| Example 38- | 24 5-FU | 0–6 MTX |
| Example 39- | 24 5-FU | 6–12 MDAM |
| Example 40- | 24 5-FU | 6–12 MTX |
| Example 41- | 24 5-FU | 12–18 MDAM |
| Example 42- | 24 5-FU | 12–18 MTX |
| Example 43- | 24 5-FU | 18–24 MDAM |
| Example 44- | 24 5-FU | 18–24 MTX |
| Example 45- | 24 5-FU | 0–12 MDAM |
| Example 46- | 24 5-FU | 0–12 MTX |
| Example 47- | 24 5-FU | 12–24 MDAM |
| Example 48- | 24 5-FU | 12–24 MTX |

TABLE 4

| Example # | 1000 nM | 100 nM | 10 nM |
|---|---|---|---|
| 37 | 29.0 | 35.1 | 49.3 |
| 38 |  | 24.2 | 58.5 |
| 39 | 30.3 | 35.2 | 46.8 |
| 40 |  | 21.1 | 55.6 |
| 41 | 30.0 | 33.7 | 46.4 |
| 42 |  | 21.9 | 51.6 |
| 43 | 36.9 | 42.3 | 51.5 |
| 44 |  | 32.6 | 56.2 |
| 45 | 16.0 | 18.8 | 35.9 |
| 46 |  | 9.3 | 53.8 |
| 47 | 22.3 | 26.5 | 50.6 |
| 48 |  | 15.6 | 57.3 |

EXAMPLES 49–64
Treatment with 48 Hours MDAM or MTX and 12 Hours. 24 Hours or 48 Hours 5-FU The following examples explore the effects of varied exposure times to 5-FU, and a continuous exposure to MDAM or MTX. The 12 and 24 hour treatments with 5-FU (Examples 49–60) explored the effects of adding the 5-FU at varying intervals. The 48 hour treatments of 5-FU involved incremental addition of MDAM (MTX) as follows: Examples 61–62 illustrate the effects of treating the cells with 70% of the final concentration of MDAM (MTX) for the first 12 hours, then adding the remaining 30% of drug at the 12 hour mark. Examples 63–64 illustrate the effects of treating with MDAM (MTX) for 36 hours at 70%, then adding the remainder. All cells assayed were HCT8/WT, and three concentrations of MDAM or MTX were assayed (10 nM, 5 nM, 1 nM), with a single concentration of 5-FU (10 $\mu$M).

| Example 49- | 48 MDAM | 0–12 5-FU |
| Example 50- | 48 MTX | 0–12 5-FU |
| Example 51- | 48 MDAM | 12–24 5-FU |
| Example 52- | 48 MTX | 12–24 5-FU |
| Example 53- | 48 MDAM | 24–36 5-FU |
| Example 54- | 48 MTX | 24–36 5-FU |
| Example 55- | 48 MDAM | 36–48 5-FU |
| Example 56- | 48 MTX | 36–48 5-FU |
| Example 57- | 48 MDAM | 0–24 5-FU |
| Example 58- | 48 MTX | 0–24 5-FU |
| Example 59- | 48 MDAM | 24–48 5-FU |
| Example 60- | 48 MTX | 24–48 5-FU |
| Example 61- | 48 MDAM (12 @ 0.7, 36 @ 1.0) | 48 5-FU |
| Example 62- | 48 MTX (12 @ 0.7, 36 @ 1.0) | 48 5-FU |
| Example 63- | 48 MDAM (24 @ 0.7, 24 @ 1.0) | 48 5-FU |
| Example 64- | 48 MTX (24 @ 0.7, 36 @ 1.0) | 48 5-FU |

TABLE 5

| Example | 10 nM | 5 nM | 1 nM |
|---|---|---|---|
| 49 | 31.6 | 48.7 | 72.5 |
| 50 | 44.7 | 79.0 | 75.4 |
| 51 | 32.4 | 58.3 | 79.2 |
| 52 | 50.3 | 78.2 | 80.7 |
| 53 | 25.2 | 54.0 | 85.1 |
| 54 | 44.4 | 86.2 | 80.5 |
| 55 | 21.2 | 43.4 | 88.4 |
| 56 | 33.7 | 88.1 | 84.4 |
| 57 | 34.4 | 46.9 | 56.0 |
| 58 | 43.9 | 55.7 | 51.9 |
| 59 | 18.5 | 40.6 | 57.9 |
| 60 | 33.1 | 65.6 | 62.0 |
| 61 | 20.3 | 28.7 | 37.7 |
| 62 | 23.7 | 36.7 | 35.7 |
| 63 | 24.9 | 31.4 | 35.0 |
| 64 | 29.6 | 35.3 | 34.1 |

EXAMPLES 65–80

Treatment of HCT/DW2 Cell Line With Hours MDAM/MTX and 12, 24 or 48 Hours 5-FU

The following examples involved the same concentrations and time exposures as Examples 49–64, and examined the effects of each against the HCT/DW2 cell subtype.

| Example 65- | 48 MDAM | 0-12 5-FU |
| Example 66- | 48 MTX | 0–12 5-FU |
| Example 67- | 48 MDAM | 12–24 5-FU |
| Example 68- | 48 MTX | 12–24 5-FU |
| Example 69- | 48 MDAM | 24–36 5-FU |
| Example 70- | 48 MTX | 24–36 5-FU |
| Example 71- | 48 MDAM | 36–48 5-FU |
| Example 72- | 48 MTX | 36–48 5-FU |
| Example 73- | 48 MDAM | 0–24 5-FU |
| Example 74- | 48 MTX | 0–24 5-FU |

-continued

| Example 75- | 48 MDAM | 24–48 5-FU |
| Example 76- | 48 MTX | 24–48 5-FU |
| Example 77- | 48 MDAM (12 @ 0.7, 36 @ 1.0) | 48 5-FU |
| Example 78- | 48 MTX (12 @ 0.7, 36 @ 1.0) | 48 5-FU |
| Example 79- | 48 MDAM (24 @ 0.7, 24 @ 1.0) | 48 5-FU |
| Example 80- | 48 MTX (24 @ 0.7, 36 @ 1.0) | 48 5-FU |

TABLE 6

| Example | 10 nM | 5 nM | 1 nM |
|---|---|---|---|
| 65 | 25.0 | 34.9 | 73.8 |
| 66 | 47.2 | 81.7 | 76.3 |
| 67 | 22.4 | 37.4 | 83.9 |
| 68 | 50.8 | 78.4 | 77.9 |
| 69 | 17.1 | 27.3 | 77.6 |
| 70 | 41.0 | 75.8 | 77.4 |
| 71 | 14.3 | 22.4 | 75.4 |
| 72 | 30.8 | 72.1 | 80.7 |
| 73 | 26.8 | 39.2 | 60.6 |
| 74 | 46.4 | 60.3 | 61.6 |
| 75 | 16.3 | 26.3 | 65.4 |
| 76 | 36.2 | 66.5 | 65.6 |
| 77 | 18.9 | 25.0 | 36.1 |
| 78 | 28.2 | 39.8 | 37.3 |
| 79 | 19.6 | 26.8 | 36.7 |
| 80 | 30.0 | 37.3 | 39.1 |

The examples demonstrate the synergistic effects of combinations of MDAM with either 5-FU, UFT, or S-1 against three different cell lines as compared to the treatment of these lines with a single drug. Exact dosages and treatment regimens will depend on the individual case facts. The invention is not intended to be limited to the above disclosures, which are presented for illustrative purposes only.

What is claimed is:

1. A method of treating cancer in mammals comprising administering a synergistic effective amount of a combination of two compounds to a patient in need of such treatment, wherein a first of said two compounds is γ-methylene-10-deazaaminopterin, and said second compound is 5-FU, wherein the weight to weight ratio of 5-FU to γ-methylene-10-deazaaminopterin is synergistic.

2. The method of claim 1 wherein the γ-methylene-10-deazaaminopterin is administered first, followed by the 5-FU.

3. The method of claim 1 wherein the 5-FU is administered first, followed by the γ-methylene-10-deazaaminopterin.

4. The method of any of claims 1, 2 or 3 wherein the γ-methylene-10-deazaaminopterin is administered in amounts sufficient to generate at least 1 nM concentrations in the body, and the 5-FU is administered in amounts sufficient to generate at least 1 μM concentrations in the body.

* * * * *